(12) United States Patent
Takamine et al.

(10) Patent No.: US 7,981,458 B2
(45) Date of Patent: Jul. 19, 2011

(54) FOOD MATERIAL AND FOOD PRODUCT USING THE SAME

(75) Inventors: Kazuhiro Takamine, Funabashi (JP); Masanori Hirayama, Fukuoka (JP); Kazuhide Kato, Funabashi (JP); Takanobu Shibuta, Fukuoka (JP)

(73) Assignee: The Torigoe Co., Ltd. (JP)

( * ) Notice: Subject to any disclaimer, the term of this patent is extended or adjusted under 35 U.S.C. 154(b) by 829 days.

(21) Appl. No.: 11/682,644

(22) Filed: Mar. 6, 2007

(65) Prior Publication Data

US 2008/0113079 A1 May 15, 2008

(30) Foreign Application Priority Data

Nov. 10, 2006 (JP) ................................ 2006-305848
Dec. 7, 2006 (JP) ................................ 2006-330437

(51) Int. Cl.
*A23L 1/05* (2006.01)

(52) U.S. Cl. .......... 426/573; 426/19; 426/446; 426/482; 426/629; 426/654; 426/660

(58) Field of Classification Search .................. 426/19, 426/629, 654, 482, 573, 660, 446
See application file for complete search history.

(56) References Cited

U.S. PATENT DOCUMENTS

| 2005/0196515 A1 | 9/2005 | Araki et al. |
| 2005/0276896 A1 | 12/2005 | Sadek et al. |

FOREIGN PATENT DOCUMENTS

| DE | 2831729 A1 | 2/1979 |
| DE | 2837294 A1 | 3/1979 |
| GB | 2022391 A | 12/1979 |
| JP | 57-125642 A | 8/1982 |
| JP | 59-15604 B2 | 4/1984 |
| JP | 61-181333 A | 8/1986 |
| JP | 62-22540 A | 1/1987 |
| JP | 04-023942 A | 1/1992 |
| JP | 10-191873 A | 7/1998 |
| JP | 2001-128637 A | 5/2001 |
| JP | 2004-024187 A | 1/2004 |
| JP | 2004-041014 A | 2/2004 |
| JP | 2004-357631 A | 12/2004 |
| JP | 3687049 B1 | 6/2005 |
| JP | 3692199 B2 | 6/2005 |
| JP | 2005-245321 A | 9/2005 |
| WO | 03049545 A1 | 6/2003 |

OTHER PUBLICATIONS

The Daily Gullet, p. 1, Sesame havah (scott111123), Apr. 4, 2004, (http://formums.egullet.org/index.php?topic/40614-sesame-havah/pages 1-12 (Nov. 27, 2009).*
"The Herbs Place", www.theherbsplace.com/Psyllium_Hulls_Combination_powder_13_Oz._p._75.html, 1998-2019, pp. 1-3.*
Extended search report issued in corresponding European patent application No. 07004448.2-2114, dated Jan. 21, 2008.
Relevant Portions of Japanese Office Action, which is a Notice of Rejection, issued in the basic Japanese Patent Application No. 2006-330437, dated Feb. 20, 2007.

* cited by examiner

*Primary Examiner* — Helen F Heggestad
(74) *Attorney, Agent, or Firm* — Rossi, Kimms & McDowell LLP

(57) ABSTRACT

Provided is a food material which contains, as its main ingredients, a wheat protein and at least one of a fusuma bran and a nuka bran, and which eliminates a poor texture peculiar to the fusuma bran, the nuka bran, and a mixture of the fusuma bran and the nuka bran. For this purpose, the food material contains a thickening stabilizer as well as a wheat protein and at least one of a roasted fusuma bran and a roasted nuka bran.

6 Claims, No Drawings

FOOD MATERIAL AND FOOD PRODUCT USING THE SAME

BACKGROUND OF THE INVENTION

1. Field of the Invention

The present invention relates to a food material and to a food product using such a food material.

2. Description of the Related Art

It is known that obesity and lifestyle-related diseases such as diabetes and hyperlipemia can be prevented by consuming food products of starchy carbohydrate, for example, rice and wheat flour, as little as possible. A known example of food materials with less content of carbohydrate contains, as its major ingredients, gluten, psyllium husk powder, and roasted wheat bran or roasted rice bran (see JP3687049B). Other known examples are bread containing wheat flour and roasted wheat bran (see JP SH062-22540A), and bread mix containing wheat flour, wheat bran powder and granulated wheat bran (see JP3692199B).

In the food material described in JP3687049B, the wheat bran or the rice bran is roasted to mask the peculiar grainy smell. However, the fact that the food material does not contain wheat flour, brings about the insufficient body formation, which, in turn, adversely affects the appearance of food products in a case where fermentation process by yeast is involved in the making of the food products such as bread. Specifically, the dough made from the food material not containing wheat flour does not rise during fermentation, or the insufficient breaking takes place in such dough, so that the bread does not rise when baked. In addition, the texture of the bread made from the above-mentioned food material is far from the ordinary bread on the market. Moreover, the quality of the bread described in JP SH062-22540A and the quality of the bread mix described in JP3692199A are not satisfactory. Furthermore, these food materials are wheat-flour-based food materials with addition of wheat bran, so that the food products produced from such food materials contain a lot of wheat flour. As a result, restriction of carbohydrate content cannot be achieved with such food products.

The present invention was proposed in view of the above-mentioned problems. An object of the present invention is to provide a food material which contains wheat protein and at least one of fusuma bran (bran of wheat or the like) and nuka bran (bran of rice or the like), and which eliminates the poor texture peculiar to the fusuma bran, the nuka bran or a mixture of these two types of bran. Another object of the present invention is to provide a food product using such a food material.

SUMMARY OF THE INVENTION

A food material according to a first aspect of the present invention to accomplish the above-mentioned objects is characterized by containing wheat protein, a thickening stabilizer and at least one of fusuma bran and nuka bran. The thickening stabilizer includes a substance that has a certain viscous force and a high swelling capacity in cold water.

A food material according to a second aspect of the present invention to accomplish the above-mentioned objects is the food material according to the first aspect of the present invention, and, in addition, is characterized in that the thickening stabilizer contains at least one of gellan gum, galactomannan, glucomannan, karaya, gum, methyl cellulose and carboxymethyl cellulose.

A food material according to a third aspect of the present invention to accomplish the above-mentioned objects is the food material according to the first aspect, and, in addition, is characterized by further containing fiber.

A food material according to a fourth aspect of the present invention to accomplish the above-mentioned objects is the food material according to the third aspect, and, in addition, is characterized in that the fiber is citrus fiber.

A food material according to a fifth aspect of the present invention to accomplish the above-mentioned objects is the food material according to the first aspect, and, in addition, is characterized by further containing lactic acid ferment.

A food material according to a sixth aspect of the present invention to accomplish the above-mentioned objects is the food material according to the fifth aspect, and, in addition, is characterized in that the lactic acid ferment is a powder made by drying and powderizing microorganisms cultured in a wheat-flour-dough medium. The microorganisms belong to yeast *Saccharomyces exiguus*, and lactic acid bacteria *Lactobacillus sanfrancisco*.

A food product according to a seventh aspect of the present invention to accomplish the above-mentioned objects is any one of bread and confectionery, and is characterized by being made by baking dough prepared by adding sesame paste to the food material according to the first aspect of the present invention.

The food material according to the present invention contains wheat protein, a thickening stabilizer and at least one of fusuma bran and nuka bran. Accordingly, obtained with such a food material is a food product, such as bread, which is excellent in its texture and volume. In addition, the food material basically contains no carbohydrate (for example, starch, wheat flour, rice flour, etc.), so that the food material has a nutritional importance as a carbohydrate-restricted diet. Accordingly, such a food material can be used in a food product for preventing obesity and lifestyle-related diseases, such as diabetes and hyperlipemia.

DETAILED DESCRIPTION OF THE INVENTION EMBODIMENT

A preferred embodiment of a food material and a food product using such a food material according to the present invention will be described in detail below.

A food material according to the preferred embodiment of the present invention is characterized by containing wheat protein, a thickening stabilizer and at least one of fusuma bran and nuka bran. Specifically, main ingredients of the food material are wheat protein and at least one of fusuma bran and nuka bran. Basically, no carbohydrate is contained in the food material, except for a tiny quantity of carbohydrate that adheres to the fusuma bran or to the nuka bran. The food material containing only these constituent ingredients is made into dough with no addition of wheat flour, of barley flour, or of starch. Accordingly, dough that is made with an increased amount of at least one of fusuma bran and nuka bran has an inferior hydration force and an inferior elasticity. Consequently, the dough is formed insufficiently. Such insufficiently-formed dough easily lets out the water that has once been taken in. A food product made from such dough has a stiff and dry texture. Dough that is made with an increased amount of wheat protein becomes a stiff and elastic mass with less viscosity, so that soft net structure (network) by gluten is not achieved. In addition, the dough made from the food material as described in JP3687049B, which contains gluten, psyllium husk powder and roasted wheat bran or roasted rice bran as main ingredients, becomes moist, and has a good water-retention property, but the soft net structure by gluten is not necessarily achieved. Then, a thickening stabilizer is mixed with the food material containing the above-mentioned constituent ingredients. Accordingly, the dough made from this food material has an improved viscosity and an improved water-retention property, becomes moist. Furthermore, the connection of gluten is assisted, and the formation of the net structure is promoted. Use of a substance with a certain viscous force and a high swelling capacity in cold water, among various thickening stabilizers, further improves the hydration force and the gel strength, and the net structure by gluten is firmly formed. The volume, the oven spring and the moisturizing property of the bread, are also improved (a not-dry, soft texture of the bread is obtained). Use of at least one of, for example, gellan gum, galactomannan, glucomannan, karaya gum, methyl cellulose and carboxymethyl cellulose has the above-mentioned effects. Furthermore, when a thickening stabilizer with a high viscous force, such as xanthan gum, is used together with the above-mentioned substance, a soft net structure is formed and the moisturizing effect is further enhanced.

When powder of fiber, preferably of citrus fiber, is added to the recipe, the dough made from this food material shows a great improvement in its water-absorption ability and in its water-retention ability. Moreover, addition of lactic acid ferment to the food material helps the enzyme produced by microorganisms in the ferment act on the dough to improve the extensibility of dough, and strengthens the net structure by gluten. Furthermore, since the protein of gluten and the like is degraded into peptides, or amino acids, umami (savory taste) is improved.

The wheat protein is called gluten, and its main contents are gliadin and glutenin. Fusuma bran is the epidermis portion of wheat or rye grain. Nuka bran is the epidermis portion, embryo, and cell walls of rice, barley, oat, pearl barley and naked barley, and is produced when these grains are milled. In the present invention, however, the food material is prepared to be a carbohydrate-restricted diet, so that the carbohydrate (starch, rice flour, barley flour, etc.) contained in nuka bran is separated in advance through processes such as classification and sieving.

Ordinary fusuma bran and nuka bran contain microorganisms such as bacteria, yeast and fungi as well as oxidative enzymes such as polyphenol oxydase, so that the kind of fusuma bran and the kind of nuka bran are not suitable, as they are, for food products. Accordingly, in the above-mentioned fusuma bran and nuka bran of the present invention, microorganisms are sterilized and enzymes are deactivated. Examples of drying method include hot-air drying, cold-air drying, spray drying and freeze drying. Some drying processes adversely affect the final products as an uncomfortable smell of fusuma bran and of nuka bran is left. Thus, the fusuma bran and nuka bran are preferably processed through a roasting process. Usually, the roasting is carried out at 100° C. or higher, but there is no particular limitation on the conditions such as how high the temperature is and how long the roasting continues. With these processes, microorganisms are sterilized, enzymes are deactivated, and the grainy smell peculiar to the brans is masked. At least one of the fusuma bran and of the nuka bran may be pulverized into powder by a grinding machine or the like after the bran is dried.

The proportion of at least one of fusuma bran and nuka bran to wheat protein is not particularly limited to a certain value. It is noted, however, that, when dough made from the food material in which the proportion of at least one of fusuma bran and nuka bran is exceeds 80% or higher within the food material is baked, the bread does not rise and becomes flat in shape. In contrast, when the proportion of wheat protein exceeds 80% or higher within the food material, the elasticity of the dough made from this food material increases more than necessarily and becomes too stiff. There is no particular limitation on the above-mentioned proportions. Nevertheless, the above description indicates that any proportions will be allowed as long as the proportion of at least one of fusuma bran and nuka bran may be no more than 80% within the food material and at the same time the proportion of wheat protein may be no more than 80% within the food material in the present invention.

To 100 parts by weight (from now on, simply referred to as "parts") mixture of wheat protein and at least one of fusuma bran and nuka bran, a preferable amount of each of thickening stabilizer and fiber is from 0.01 parts to 10 parts, inclusive. Fiber cannot express its water-retention ability when less than 0.01 parts thereof is used. On the other hand, more than 10 parts of fiber makes too much water be absorbed in the dough. The too much water thus absorbed makes the total composition unbalanced, and the resultant food product is far from appropriate. In addition, the thickening stabilizer cannot express its viscosity when less than 0.01 parts thereof is used. On the other hand, more than 10 parts of thickening stabilizer renders the viscosity of the dough too high. The too high viscosity renders the dough incoherent, so that a suitable consistency (stiffness of dough) is never obtainable. Accordingly, the compounding ratio (from 0.01 parts to 10 parts each to 100 parts mixture) enables the water-retention property to be expressed suitably, and, at the same time, improves the viscosity.

Examples of the thickening stabilizers include: viscous substances derived from vegetable seeds such as guar gum, tara gum, cassia gum, tamarind seed gum, locust bean gum and konjac mannan; viscous substances derived from vegetable resins such as arabic gum, tragacanth gum, karaya gum and ghatti gum; viscous substances derived from vegetable fruits such as pectin and arabinogalactan; and viscous substance produced by microorganisms such as xanthan gum, pullulan, dextran and gellan gum. Also included are: polysaccharides derived from seaweed such as carrageenans, alginic acid, sodium alginate, propylene glycol alginate, furcellaran, agar and curdlan; and celluloses such as carboxymethyl cellulose (CMC), methyl cellulose (MC), micro-fibrillated cellulose and seaweed cellulose.

Gellan gum is a polysaccharide produced extracellularly by a microorganism, specifically, *Sphingomonas elodea*. The gellan gum is a heteropolysaccharide with straight-chain structure, and composed of a unit of four saccharides, specifically, glucose, glucuronic acid, glucose and rhamnose, and has a carboxyl group derived from glucuronic acid. There are two types of gellan gum, i.e. deacylated gellan gum and high-acyl gellan gum. Though both of the two types have effects targeted in the present invention, high-acyl gellan gum is preferable. Deacylated gellan gum is produced by recovery of what is deacylated through fermentation process by microorganisms. On the other hand, high-acyl gellan gum is produced by recovery of fermenting substance in the stage prior to deacylation. In high-acyl gellan gum, glyceryl group and acetyl group are located on the same glucose residue of main chain of deacylated gellun gum. Examples of high-acyl gellan gum are: Kelcogel® HM, Kelcogel® HT, Kelcogel® LT100, all of which are commercialized by CP Kelco. As these products differ in synersis, transparency, and optimum pH, they have different names. Nevertheless, all of these products fit for the purpose of the present invention. Note that what is called "native gellan gum" and high-acyl gellan gum are the same. Normally, high-acyl gellan gum and deacylated gellan gum are insoluble in cold water, so that gelation thereof needs preheating up to 80° C. or higher before dissolution. Regarding the characteristics shown by these two gellan gums at the time of gelation, it is reported that high-acyl gellan gum expresses a soft elasticity like gelatin, while deacylated gellan gum forms a stiff and fragile gel like agar. These characteristics affect the volume, smoothness (texture) of the products having been subjected to the final baking (heating) process, but are not essential for the present invention. Characteristics that are found out to be essential for the present invention are that both high-acyl gellan gum and dehydrated gellan gum are insoluble in cold water, but that both gellan gums show a cold-water swelling capacity, which is extremely characteristic. In addition, the cold-water swelling capacity of the high-acyl gellan gum is significantly higher than that of the deacylated gellan gum. The cold-water swelling capacity brings about an easy intake of water in the dough when the mixture of wheat protein and at least one of fusuma bran and nuka bran is added with water and mixed. Then, formation of net structure by gluten is promoted. Thus, the cold-water swelling capacity significantly affects the volume of the final product. A high tolerance to freezing and thawing and an anti-syneresis effect, both of which are characteristics of high-acyl gellan gum, but not those of deacylated gellan gum, are significantly effective when the products are refrigerated and stored after the final baking. This contributes to the objects of the present invention.

Galactomannans are polysaccharides composed of a (1-4)-linked beta-D-mannose main chain with 1-6-linked alpha-D-galactose side chains. Representative thickening stabilizers of galactomannans include guar gum, tara gum and locust bean gum. Guar gum is made from guar, which is a legume plant mainly grown mainly in South Asia. Tara gum is made from tara (*Caesalpinia spinosa*) grown in South America, precisely, in Peru etc. Locust bean gum is made from seeds of the Carob tree, which is an evergreen tree grown only in hot and dry climate of the Mediterranean region. These gums are produced in powder from purified endosperm of respective seeds. As described above, galactomannans are polysaccharides composed of a (1-4)-linked beta-D-mannose main chain with 1-6-linked alpha-D-galactose side chains. In guar gum, specifically, two mannoses are linked to each galactose. In tara gum, three mannoses are linked to each galactose. In locust bean gum, four mannoses are linked to each galactose. Glucomannan is a main constituent of konjac, and is a complex polysaccharide with a multiple-linked structure composed of β-1, 4-linked D-glucose and D-mannose. Water solution of glucomannan shows a higher viscosity than that of galactomannan. Both galactomannan and glucomannan dissolve easily in cold water and swell considerably, while each has a high water-retention property. As the above-mentioned gellan gum, galactomannan and glucomannan contribute to improvement in formation of net structure by gluten, and in volume and texture of final products. Locust bean gum used alone shows lesser swelling capacity in cold water. However, when locust bean gum is used together with kappa-carrageenan or xanthan gum, a synergy effect is developed, and the locust bean gum swells in cold water and forms gel as in the case of guar gum or tara gum.

A known example of karaya gum is a sterculia gum, which is a sap of Karaya tree (*Sterculia urens*) of Sterculiaceae family, grown in central and northern India. Karaya gum is a polysaccharide with a structure composed of galactose, rhamnose, and galacturonic acid, which are located on the main chain, and of glucuronic acid linked to the side chain. A structure of the karaya gum including acetyl group is similar to that of high-acyl gellan gum, and shows a cold-water swelling capacity and a high gelation property, which are similar to those of high-acyl gellan gum. The viscosity of 1% solution of karaya gum is approximately 3300 mPa·s, but, in an alkaline state, the viscosity increases. A slight acetic acid smell that karaya gum has requires use of karaya gum in a limited amount and a process of mitigating the acetic acid smell. Nevertheless, karaya gum, as in the case of gellan gum or tara gum, contributes to the formation of net structure by gluten, and to improvement in the volume and the texture of final product. Additionally, tragacanth gum is a thickening stabilizer of viscous substance as in the case with karaya gum. Tragacanth gum is a polysaccharide obtained by drying the secretion of tragacanth, a legume plant. When tragacanth gum is added, the product maintains its shape better than otherwise. These gums are food additives usually used as shape-maintaining agent for sugar craft or used for decorative purpose such as for sugar paste, but these gums can be used for the purpose of the present invention.

Methyl cellulose is a nonionic, water-soluble cellulose ether, and is made from cellulose (pulp) which is widely found in nature. After the caustic soda treatment, the treated pulp is reacted with methyl chloride and etherifying agent, and thus methyl cellulose is produced. Similar substances, such as sodium (or calcium) carboxymethylcellulose, cellulose sodium (or calcium) glycolate, starch sodium glycolate, starch sodium phosphate ester, sodium polyacrylate serve as thickening stabilizers of the present invention (n.b. not more than 0.2% of food product can be used).

Cellulose has a lot of hydrophilic hydroxyl groups, which are bound with one another by strong intermolecular hydrogen binding among the hydroxyl groups to form a crystal structure. Accordingly, no water can enter between molecules of cellulose. As a result, cellulose, as it is, cannot dissolve in water. Methyl cellulose is made by substituting part of a hydrogen atom in a hydroxyl group of cellulose with a methyl group. Carboxymethyl cellulose is made, likewise, by substituting part of a hydrogen atom in a hydroxyl group of cellulose with a carboxymethyl group. The above-mentioned celluloses have similar properties. When at least one kind thereof is used in combination, the celluloses serve for the purpose of the present invention. Specifically, the celluloses dissolve in cold water easily. The water solution gelates when heated to a certain temperature or higher, and returns to the original state of solution when cooled. These properties, that is, solubility in cold water, high viscosity, and high water-retention capacity, contribute to formation of net structure by gluten, to oven spring, and to volume of final products. Though there are methyl celluloses of different grades based on viscosity, any methyl cellulose can serve for the purpose of the present invention. Nevertheless, preferable is a methyl cellulose with a viscosity of 100 mPa·s or higher in 2% solution. A methyl cellulose with a viscosity of lower than 100 mPa·s has an inferior gelation capacity and an inferior water-retention capacity, so that use of such a methyl cellulose results in a reduced gluten-membrane formation capacity, a reduced body-formation capacity, a reduced oven spring, and a reduced volume of final products. There is a usage restriction on methyl celluloses and the above-mentioned similar substances, which must be used, in total, not more than 2% of the food product. Another cellulose, hydroxypropyl methylcellulose, has the same properties as mentioned above. Though hydroxypropyl methylcellulose can be used only for food with health claims—capsules or pills—in Japan, it can be used for ordinary food in the United States.

The cold-water swelling capacity, gelation capacity and easy-to-hydrate property, all of which are brought about by at least one of gellan gum, glucomannan, karaya gum, methyl cellulose, and carboxymethyl cellulose, have an extraordinary effects when the present invention is carried out regarding food products whose main ingredients are wheat protein and at least one of fusuma bran and nuka bran. The involvement of these substances compensates for the insufficient hydration force of at least one of fusuma bran and nuka bran, and remedies the stiff elasticity by wheat protein. As a result, soft elasticity and easy-to-hydrate property, which are in contrast to the above-mentioned properties, are brought about. Moreover, better effects of these substances are expressed when the substances are used together with the above-mentioned thickening stabilizers with a high hydration force. In this case, a preferable amount of these substances added to food material containing wheat protein and at least one of fusuma bran and nuka bran is from 0.01 parts to 10 parts, inclusive. As the viscosity (mPa·s) of the water solution varies depending upon the grade, this is not a categorical limitation on the added amount of these substances. When less than 0.01 parts of these additives are used, the consistency (stiffness of dough) and easy-to-hydrate property, both to a certain degree, cannot be expressed. On the other hand, more than 10 parts of these additives makes the gel strength increased and the dough too stiff. Accordingly, the amount of addition of at least one of gellan gum, galactomannan, glucomannan, karaya gum, methyl cellulose, and carboxymethyl cellulose, should be set in the above-mentioned range, so that the consistency suitable for bread-making or confectionery-making can be expressed.

Examples of fibers other than the above-mentioned citrus fiber include: guar fiber, apple fiber, wheat fiber, barley fiber, rye fiber, beet fiber, soy fiber, carrot fiber, orange fiber, bamboo fiber, cotton-seed fiber, tomato fiber, oat fiber, and cellulose. In other words, any dietary fiber may be used for this purpose.

In this case, the above-mentioned citrus fiber is made by squeezing citrus fruits, such as oranges, then removing the juice from the squeezed liquid, and giving a high impact to the cell walls that have passed through a powderizing process. Thus, the micellar structure of the citrus fiber cells breaks, so that the citrus fiber has a porous structure, allowing a significantly increased amount of water to be absorbed. At the same time, the citrus fiber links better with water, resulting in an improved property of retaining water that has been taken in. Specifically, 2.32-ml water is absorbed per 1 g oat fiber added; 2.48 ml for soy fiber; and 4.86 ml for wheat fiber. In the case of citrus fiber, however, no less than 9.95-ml water is absorbed. In other words, a high water-absorbing capacity is expressed. Incidentally, citrus fiber is high in the water-retention capacity, which is different from wheat fiber or the like, and is also high in linking property with fat. Accordingly, use of citrus fiber, as a substitute for fat, in confectionery such as doughnuts and muffins, and in grain bread with an improved water-absorbing capacity is reported in the United States. What is found out in the present invention is that the citrus fiber involves in the body formation of a food product such as bread containing no carbohydrate (starch, wheat flour, rice flour and the like), as a substitute for the carbohydrate necessary for the body formation. In addition, use of citrus fiber together with the above-mentioned thickening stabilizer further increases the water-absorbing capacity and the water-retention capacity. Accordingly, citrus fiber serves as making the formation of gluten progress smoothly. For example, when 1-g citrus fiber is alone used, the amount of water absorbed is 9.95 ml. When use of 1-g citrus fiber with addition of 0.5-g guar gum makes the amount of water absorbed increase up to 13.35 ml.

Lactic acid ferment is produced by symbiotic microorganisms of yeast (*Saccharomyces exiguus*) and several species of lactic acid bacteria, such as *Lactobacillus sanfrancisco*. Enzymes secreted by these yeast and lactic acid bacteria act for strengthening the net structure by gluten, and thus an improved rising of dough is brought about. Umami is also improved as the strong enzymes help the degrading of proteins such as gluten into peptides and amino acids. Accordingly, the combined use of the yeast increases synergistically the maturing and fermenting power to improve the flavor and scent. At the same time, gas-generating power becomes larger. This has an effect of making the fermented food, such as bread, with a increased volume. The lactic acid ferment is made by fermenting dough from 100 parts wheat flower with addition of 50 parts water and of the above-mentioned original ferment, and they by fermenting the dough. The ferment thus produced is freeze-dried according to its purposes, and the yeast and the lactic acid bacteria can be preserved alive. In addition, the wheat-flour content in the lactic acid ferment is 67%. Addition of the ferment, to the food material, in an amount of 5% thereof is equivalent to that of wheat-flour in an amount of 3.35% of the food material. The food material is made into a food product while the additive amount of ferment is controlled. Accordingly, the ferment is used in food products that can serve to prevent obesity and life-style related diseases such as diabetes and hyperlipemia, while the food product has a nutritional value as a carbohydrate-restricted diet. In this case, the amount of the lactic acid ferment added to the food materials is from 1 part to 10 parts, inclusive. An addition of more than 10 parts lactic acid ferment has a higher effect of improvement (strengthening the net structure by gluten and improving umami) according to the amount added. Nevertheless, the effects as carbohydrate-restricted diet are reduced, in which as less amount of carbohydrate as possible is digested. An addition of less than 1 part lactic acid ferment reduces effects of strengthening the net structure by gluten and improving umami. Accordingly, the addition of the lactic acid ferment is controlled to the above-mentioned amount. Thus, a balanced expression of effects can be obtained between the effects of the strengthening the net structure by gluten and improving umami, and the effects as carbohydrate-restricted diet.

The descriptions thus far show that problems in the processes of making bread with no carbohydrate (starch) being contained can be solved. Specifically the problems are as follows. A reduced formation power of gluten at the time of mixing adversely affects the machinability at a later time to make the dough unsuitable for a manufacturing process in which the dough is transferred with manufacturing lines. Additionally, the dough does not rise in the final stage of fermentation, and the insufficient breaking takes place in such dough when baked resulting in a reduction of the volume of the bread. These problems can be solved by use of wheat protein, a thickening stabilizer and at least one of fusuma bran and nuka bran together. A preferable thickening stabilizer is gellan gum, galactomannan, glucomannan, karaya gum, methyl cellulose, or carboxymethyl cellulose. Moreover, what is found out is that use of citrus fiber together with a food material containing the above-mentioned ingredients can further solve the problems that dough does not rise in the final stage of fermentation, and that the insufficient breaking takes place in such dough when baked resulting a reduction of the volume of the bread. Furthermore, what is found out is that use of lactic acid ferment together with the food material containing these ingredients strengthens the net structure by gluten and improves umami.

In addition, what is found out is that, as a improvement measure in view of flavor, scent and nutrition, addition of sesame paste makes a big difference. Sesame contains a rich variety of nutrients, such as sesame lignan, which is an antioxidant component, so that sesame is an optimal material for health, especially suitable for antiaging. When sesame is added, flavor and scent are increased, and the unpleasant smell of fusuma bran and nuka bran can be masked. Moreover, the carbohydrate content in sesame is only 5.9%, which is a low content of carbohydrate among grains, beans and nuts. For example, the domestically-produced whole-wheat meal, often used as a material for health, has a 61.1% carbohydrate content, and domestically-produced soy bean has a 11.1% carbohydrate content (see *Standard Tables of Food Composition in Japan,* 2002 Revised Edition).

Bread-like food products according to the present invention can be obtained with ease as follows. As described thus far, the food materials to be used for the purpose are: the food material containing wheat protein, a thickening stabilizer, and at least one of fusuma bran and nuka bran; the food material in which the thickening stabilizer is at least one of gellan gum, galactomannan, glucomannan, karaya gum, methyl cellulose and carboxymethyl cellulose; the food material further containing fiber; and the food material further containing lactic acid ferment. Dough is made from these food materials with addition of yeast for bread and of water, as well as of sesame paste. Then, bread-like food products according to the present invention can be manufactured by following an ordinary bread-making method such as baking using the dough. Examples of the bread-like food products are a wide variety of breads such as bread, butter rolls, hard rolls and croissants. Examples of method of manufacturing bread include the sponge dough method and the straight dough method. In a case where the straight dough method is employed, bread-like food products can be manufactured with ease following the same procedures of mixing, floor time, separation, bench time, shaping, final proof, and baking.

In the above descriptions, the food materials contain wheat protein, thickening stabilizers and at least one of fusuma bran and nuka bran. However, a food material used for the same purpose may contain, instead of these fusuma bran and nuka bran, or in addition to these, portions such as epidermis and embryo of at least one species of bean such as soy bean or adzuki (red bean), or portions such as pericarp and seed of grapes and citruses such as oranges and yuzu citrus, wheat protein and thickening stabilizers. A food material such as this has similar advantageous effects to those obtained by food materials according to the embodiment described above.

Specific descriptions of a food material and a food product using the food material according to the present invention will be given below with examples and comparative examples.

EXAMPLE 1

As Table 1 given below shows, a food material A was obtained by mixing 50 parts wheat protein with 50 parts roasted fusuma bran with the addition of 0.4% xanthan gum as a thickening stabilizer. A bread roll was obtained by adding ingredients in the following proportions to 100 parts of the food material A, and then by carrying out processes mentioned below.

| | |
|---|---|
| food material A | 100 parts |
| whole egg | 10 parts |
| butter | 5 parts |
| fresh yeast | 3 parts |
| water | 155 parts |

The ingredients, except for the butter, were mixed at a low speed for 2 minutes, then at a medium speed for 3 minutes, and then at a high speed for 1 minute. Subsequently, the mixture was further mixed with addition of the butter at a low speed for 1 minute, then at a medium speed for 3 minutes, and then at a high speed for 3 minutes, while the kneading temperature was 27° C. Furthermore, the dough was fermented at 35° C. for 30 minutes, then was divided into pieces of 70 g each, and then rest for a bench time of 25 minutes. After that, the divided dough was subjected to 60-minute final proof at 38° C. and at 85% relative humidity, and then was baked at 210° C. for 10 minutes.

EXAMPLE 2

As Table 1 given below shows, a food material B was obtained by mixing 50 parts wheat protein with 50 parts roasted fusuma bran with the addition of 0.3% high acyl gellan gum. A bread roll was obtained by adding ingredients in the following proportions to 100 parts of the food material B, and then by carrying out processes mentioned below.

| | |
|---|---|
| food material B | 100 parts |
| whole egg | 10 parts |
| butter | 5 parts |
| fresh yeast | 3 parts |
| water | 155 parts |

The ingredients, except for the butter, were mixed at a low speed for 2 minutes, then at a medium speed for 3 minutes, and then at a high speed for 1 minute. Subsequently, the mixture was further mixed with addition of the butter at a low speed for 1 minute, then at a medium speed for 3 minutes, and then at a high speed for 3 minutes, while the kneading temperature was 27° C. Furthermore, the dough was fermented at 35° C. for 30 minutes, then was divided into pieces of 70 g each, and then rest for a bench time of 25 minutes. After that, the divided dough was subjected to 60-minute final proof at 38° C. and at 85% relative humidity, and then was baked at 210° C. for 10 minutes.

EXAMPLE 3

As Table 1 given below shows, a food material C was obtained by mixing 50 parts wheat protein with 50 parts roasted barley bran with the addition of 0.4% xanthan gum as a thickening stabilizer, of 0.3% high acyl gellan gum, and of 0.8% citrus fiber. A bread roll was obtained by adding ingredients in the following proportions to 100 parts of the food material C, and then by carrying out processes mentioned below.

| | |
|---|---|
| food material C | 100 parts |
| whole egg | 10 parts |
| butter | 5 parts |
| fresh yeast | 3 parts |
| water | 155 parts |

The ingredients, except for the butter, were mixed at a low speed for 2 minutes, then at a medium speed for 3 minutes, and then at a high speed for 1 minute. Subsequently, the mixture was further mixed with addition of the butter at a low speed for 1 minute, then at a medium speed for 3 minutes, and then at a high speed for 3 minutes, while the kneading temperature was 27° C. Furthermore, the dough was fermented at 35° C. for 30 minutes, then was divided into pieces of 70 g each, and then rest for a bench time of 25 minutes. After that, the divided dough was subjected to 60-minute final proof at 38° C. and at 85% relative humidity, and then was baked at 210° C. for 10 minutes.

EXAMPLE 4

As Table 1 given below shows, a food material D was obtained by mixing 50 parts wheat protein with 50 parts roasted fusuma bran with the addition of 0.4% xanthan gum as a thickening stabilizer, of 0.3% high acyl gellan gum, of 0.8% citrus fiber, of 5% lactic acid ferment. A bread roll was obtained by adding ingredients in the following proportions to 100 parts of the food material D, and then by carrying out processes mentioned below.

| | |
|---|---|
| food material D | 100 parts |
| whole egg | 10 parts |
| butter | 5 parts |
| fresh yeast | 3 parts |
| water | 155 parts |

The ingredients, except for the butter, were mixed at a low speed for 2 minutes, then at a medium speed for 3 minutes, and then at a high speed for 1 minute. Subsequently, the mixture was further mixed with addition of the butter at a low speed for 1 minute, then at a medium speed for 3 minutes, and then at a high speed for 3 minutes, while the kneading temperature was 27° C. Furthermore, the dough was fermented at 35° C. for 30 minutes, then was divided into pieces of 70 g each, and then rest for a bench time of 25 minutes. After that, the divided dough was subjected to 60-minute final proof at 38° C. and at 85% relative humidity, and then was baked at 210° C. for 10 minutes.

EXAMPLE 5

As Table 1 given below shows, a bread roll was obtained by further adding sesame paste to the ingredients in respective proportions of the bread roll according to the method of Example 4, and then by carrying out processes mentioned below.

| | |
|---|---|
| food material D | 100 parts |
| whole egg | 10 parts |
| butter | 5 parts |
| sesame paste | 10 parts |
| fresh yeast | 3 parts |
| water | 155 parts |

The ingredients, except for the butter, were mixed at a low speed for 2 minutes, then at a medium speed for 3 minutes, and then at a high speed for 1 minute. Subsequently, the mixture was further mixed with addition of the butter at a low speed for 1 minute, then at a medium speed for 3 minutes, and then at a high speed for 3 minutes, while the kneading temperature was 27° C. Furthermore, the dough was fermented at 35° C. for 30 minutes, then was divided into pieces of 70 g each, and then rest for a bench time of 25 minutes. After that, the divided dough was subjected to 60-minute final proof at 38° C. and at 85% relative humidity, and then was baked at 210° C. for 10 minutes.

EXAMPLE 6

As Table 1 given below shows, a croissant was obtained by adding ingredients in the following proportions to 100 parts of the food material B obtained according to the method of Example 2, and then by carrying out processes mentioned below.

| | |
|---|---|
| food material B | 100 parts |
| whole egg | 10 parts |
| butter | 5 parts |
| fresh yeast | 3 parts |
| roll-in butter | 50 parts |
| water | 155 parts |

The ingredients, except for the butter, were mixed at a low speed for 2 minutes, and then at a medium speed for 3 minutes. Subsequently, the mixture was further mixed with addition of the butter at a low speed for 1 minute, and then at a medium speed for 3 minutes, while dough was cooled to make the kneading temperature be at 24° C. Furthermore, the dough was folded into thirds three times for rolling-in, and then was divided into pieces of 70 g each. After that, the divided dough was subjected to 60-minute final proof at 30° C. and at 75% relative humidity, and then was baked at 210° C. for 10 minutes.

EXAMPLE 7

As Table 1 given below shows, a food material E was obtained by adding, to the food material B obtained according to the method of Example 2, 0.4% xanthan gum, 2% citrus fiber, and 3% lactic acid ferment. A croissant was obtained by adding ingredients in the following proportions to 100 parts of the food material E, and then by carrying out processes mentioned below.

| | |
|---|---|
| food material E | 100 parts |
| whole egg | 10 parts |
| butter | 5 parts |
| fresh yeast | 3 parts |
| roll-in butter | 50 parts |
| water | 155 parts |

The ingredients, except for the butter, were mixed at a low speed for 2 minutes, and then at a medium speed for 3 minutes. Subsequently, the mixture was further mixed with addition of the butter at a low speed for 1 minute, and then at a medium speed for 3 minutes, while dough was cooled to make the kneading temperature be at 24° C. Furthermore, the dough was folded into thirds three times for rolling-in, and then was divided into pieces of 70 g each. After that, the divided dough was subjected to 60-minute final proof at 30° C. and at 75% relative humidity, and then was baked at 210° C. for 10 minutes.

EXAMPLE 8

As Table 1 given below shows, a croissant was obtained by further adding sesame paste to the ingredients in respective proportions of the croissant according to the method of Example 7, and then by carrying out processes mentioned below.

| | |
|---|---:|
| food material E | 100 parts |
| whole egg | 10 parts |
| butter | 5 parts |
| sesame paste | 10 parts |
| fresh yeast | 3 parts |
| roll-in butter | 50 parts |
| water | 155 parts |

The ingredients, except for the butter, were mixed at a low speed for 2 minutes, and then at a medium speed for 3 minutes. Subsequently, the mixture was further mixed with addition of the butter at a low speed for 1 minute, and then at a medium speed for 3 minutes, while dough was cooled to make the kneading temperature be at 24° C. Furthermore, the dough was folded into thirds three times for rolling-in, and then was divided into pieces of 70 g each. After that, the divided dough was subjected to 60-minute final proof at 30° C. and at 75% relative humidity, and then was baked at 210° C. for 10 minutes.

EXAMPLE 9

As Table 1 given below shows, a food material F was obtained by mixing 50 parts wheat protein with 50 parts roasted fusuma bran with the addition of 0.4% xanthan gum as a thickening stabilizer, of 0.3% high acyl gellan gum, of 0.1% citrus fiber, and of 1% lactic acid ferment. Cookies were obtained by adding ingredients in the following proportions to 100 parts of the food material F, and then by carrying out processes mentioned below.

| | |
|---|---:|
| food material F | 100 parts |
| whole egg | 100 parts |

-continued

| | |
|---|---:|
| butter | 90 parts |
| sesame paste | 20 parts |
| dolomite | 1 part |
| sucralose | 0.06 parts |
| acesulfame pottasium | 0.06 parts |

Dough was prepared by mixing the liquid whole egg, the butter and the sesame paste, and then further mixing completely with addition of the other ingredients. The dough was rolled out to a sheet, and cut out with a certain predetermined cookie cutter (15 g each). The cut-out dough rest for a bench time of approximately an hour, and then was baked at 180° C. for 25 minutes.

EXAMPLE 10

As Table 1 given below shows, a food material G was obtained by mixing 50 parts wheat protein with 50 parts roasted fusuma bran with the addition of 0.4% xanthan gum as a thickening stabilizer, of 0.3% high acyl gellan gum, and of 2.5% citrus fiber. Fresh udon (a thick Japanese noodle made with wheat flour) was obtained by adding 55 parts saline solution (8 wt % concentration) to 100 parts of the food material G, and then by carrying out preparation processes mentioned below.

Preparation Processes

| | |
|---|---|
| mixing | 10 minutes |
| laminating | |
| maturing | 30 minutes |
| flattening | |
| cutting | with No. 12 cutter (square), width: 2.5 mm, thickness: 1.6 mm |

TABLE 1

| | ex. No. | | | | | | | | | |
|---|---|---|---|---|---|---|---|---|---|---|
| | 1 | 2 | 3 | 4 | 5 | 6 | 7 | 8 | 9 | 10 |
| wheat protein | 50 | 50 | 50 | 50 | 50 | 50 | 50 | 50 | 50 | 50 |
| roasted fusuma bran | 50 | 50 | — | 50 | 50 | 50 | 50 | 50 | 50 | 50 |
| roasted barley bran | — | — | 50 | — | — | — | — | — | — | — |
| xanthan gum | 0.4 | — | 0.4 | 0.4 | 0.4 | — | 0.4 | 0.4 | 0.4 | 0.4 |
| high acyl gellan gum | — | 0.3 | 0.3 | 0.3 | 0.3 | 0.3 | 0.3 | 0.3 | 0.3 | 0.3 |
| citrus fiber | — | — | 0.8 | 0.8 | 0.8 | — | 2 | 2 | 0.1 | 2.5 |
| lactic acid ferment | — | — | — | 5 | 5 | — | 3 | 3 | 1 | — |
| sesame paste | — | — | — | — | 10 | — | — | 10 | 20 | — |
| | bread roll | bread roll | bread roll | bread roll | bread roll | croissant | croissant | croissant | cookie | fresh udon (noodle) |

EXAMPLE 11

As Table 2 given below shows, a food material H was obtained by mixing 50 parts wheat protein with 50 parts roasted fusuma bran with the addition of 0.3% tara gum as a thickening stabilizer. A bread roll was obtained by adding ingredients in the following proportions to 100 parts of the food material H, and then by carrying but processes mentioned below.

| food material H | 100 parts |
|---|---|
| whole egg | 10 parts |
| butter | 5 parts |
| fresh yeast | 3 parts |
| water | 155 parts |

The ingredients, except for the butter, were mixed at a low speed for 2 minutes, then at a medium speed for 3 minutes, and then at a high speed for 1 minute. Subsequently, the mixture was further mixed with addition of the butter at a low speed for 1 minute, then at a medium speed for 3 minutes, and then at a high speed for 3 minutes, while the kneading temperature was 27° C. Furthermore, the dough was fermented at 35° C. for 30 minutes, then was divided into pieces of 70 g each, and then rest for a bench time of 25 minutes. After that, the divided dough was subjected to 60-minute final proof at 38° C. and at 85% relative humidity, and then was baked at 210° C. for 10 minutes.

EXAMPLE 12

As Table 2 given below shows, a food material J was obtained by mixing 50 parts wheat protein with 50 parts roasted fusuma bran with the addition of 0.3% karaya gum as a thickening stabilizer. A bread roll was obtained by adding ingredients in the following proportions to 100 parts of the food material J, and then by carrying out processes mentioned below.

| food material J | 100 parts |
|---|---|
| whole egg | 10 parts |
| butter | 5 parts |
| fresh yeast | 3 parts |
| water | 155 parts |

The ingredients, except for the butter, were mixed at a low speed for 2 minutes, then at a medium speed for 3 minutes, and then at a high speed for 1 minute. Subsequently, the mixture was further mixed with addition of the butter at a low speed for 1 minute, then at a medium speed for 3 minutes, and then at a high speed for 3 minutes, while the kneading temperature was 27° C. Furthermore, the dough was fermented at 35° C. for 30 minutes, then was divided into pieces of 70 g each, and then rest for a bench time of 25 minutes. After that, the divided dough was subjected to 60-minute final proof at 38° C. and at 85% relative humidity, and then was baked at 210° C. for 10 minutes.

EXAMPLE 13

As Table 2 given below shows, a food material K was obtained by mixing 50 parts wheat protein with 50 parts roasted fusuma bran with the addition of 0.6% methyl cellulose (viscosity 4000 mPa·s, 2% solution) as a thickening stabilizer. A bread roll was obtained by adding ingredients in the following proportions to 100 parts of the food material K, and then by carrying out processes mentioned below.

| food material K | 100 parts |
|---|---|
| whole egg | 10 parts |
| butter | 5 parts |
| fresh yeast | 3 parts |
| water | 155 parts |

The ingredients, except for the butter, were mixed at a low speed for 2 minutes, then at a medium speed for 3 minutes, and then at a high speed for 1 minute. Subsequently, the mixture was further mixed with addition of the butter at a low speed for 1 minute, then at a medium speed for 3 minutes, and then at a high speed for 3 minutes, while the kneading temperature was 27° C. Furthermore, the dough was fermented at 35° C. for 30 minutes, then was divided into pieces of 70 g each, and then rest for a bench time of 25 minutes. After that, the divided dough was subjected to 60-minute final proof at 38° C. and at 85% relative humidity, and then was baked at 210° C. for 10 minutes.

EXAMPLE 14

As Table 2 given below shows, a food material L was obtained by mixing 50 parts wheat protein with 50 parts roasted fusuma bran with the addition of 0.4% xanthan gum, 0.3% tara gum as thickening stabilizers. A bread roll was obtained by adding ingredients in the following proportions to 100 parts of the food material L, and then by carrying out processes mentioned below.

| food material L | 100 parts |
|---|---|
| whole egg | 10 parts |
| butter | 5 parts |
| fresh yeast | 3 parts |
| water | 155 parts |

The ingredients, except for the butter, were mixed at a low speed for 2 minutes, then at a medium speed for 3 minutes, and then at a high speed for 1 minute. Subsequently, the mixture was further mixed with addition of the butter at a low speed for 1 minute, then at a medium speed for 3 minutes, and then at a high speed for 3 minutes, while the kneading temperature was 27° C. Furthermore, the dough was fermented at 35° C. for 30 minutes, then was divided into pieces of 70 g each, and then rest for a bench time of 25 minutes. After that, the divided dough was subjected to 60-minute final proof at 38° C. and at 85% relative humidity, and then was baked at 210° C. for 10 minutes.

EXAMPLE 15

As Table 2 given below shows, a food material M was obtained by mixing 50 parts wheat protein with 50 parts roasted fusuma bran with the addition of 0.1% high acyl gellan gum, 0.1% tara gum and 0.2% methyl cellulose (viscosity 4000 mPa·s, 2% solution) as thickening stabilizers. A bread roll was obtained by adding ingredients in the following proportions to 100 parts of the food material M, and then by carrying out processes mentioned below.

| | |
|---|---|
| food material M | 100 parts |
| whole egg | 10 parts |
| butter | 5 parts |
| fresh yeast | 3 parts |
| water | 155 parts |

The ingredients, except for the butter, were mixed at a low speed for 2 minutes, then at a medium speed for 3 minutes, and then at a high speed for 1 minute. Subsequently, the mixture was further mixed with addition of the butter at a low speed for 1 minute, then at a medium speed for 3 minutes, and then at a high speed for 3 minutes, while the kneading temperature was 27° C. Furthermore, the dough was fermented at 35° C. for 30 minutes, then was divided into pieces of 70 g each, and then rest for a bench time of 25 minutes. After that, the divided dough was subjected to 60-minute final proof at 38° C. and at 85% relative humidity, and then was baked at 210° C. for 10 minutes.

TABLE 2

| | Example 11 | Example 12 | Example 13 | Example 14 | Example 15 |
|---|---|---|---|---|---|
| wheat protein | 50 | 50 | 50 | 50 | 50 |
| roasted fusuma bran | 50 | 50 | 50 | 50 | 50 |
| xanthan gum | — | — | — | 0.4 | — |
| high acyl gellan gum | — | — | — | — | 0.1 |
| tara gum | 0.3 | — | — | 0.3 | 0.1 |
| karaya gum | — | 0.3 | — | — | — |
| methyl cellulose (viscosity 4000 mPa · s) | — | — | 0.6 | — | 0.2 |
| | bread roll | bread roll | bread roll | bread roll | bread roll |

COMPARATIVE EXAMPLE 1

As Comparative Example 1, a food material a was obtained by replacing the food material B of the Example 2 with a mixture of 50 parts wheat protein and 50 parts fresh fusuma bran as Table 3 given below shows. A bread roll was obtained by adding ingredients in the following proportions to 100 parts of the food material a, and then by carrying out processes mentioned below.

| | |
|---|---|
| food material a | 100 parts |
| whole egg | 10 parts |
| butter | 5 parts |
| fresh yeast | 3 parts |
| water | 155 parts |

The ingredients, except for the butter, were mixed at a low speed for 2 minutes, then at a medium speed for 3 minutes, and then at a high speed for 1 minute. Subsequently, the mixture was further mixed with addition of the butter at a low speed for 1 minute, then at a medium speed for 3 minutes, and then at a high speed for 3 minutes, while the kneading temperature was 27° C. Furthermore, the dough was fermented at 35° C. for 30 minutes, then was divided into pieces of 70 g each, and then rest for a bench time of 25 minutes. After that, the divided dough was subjected to 60-minute final proof at 38° C. and at 85% relative humidity, and then was baked at 210° C. for 10 minutes.

COMPARATIVE EXAMPLE 2

As Comparative Example 2, a food material b was obtained by replacing the food material B of the Example 2 with a mixture of 50 parts wheat protein and 50 parts roasted fusuma bran as Table 3 given below shows. A bread roll was obtained by adding ingredients in the following proportions to 100 parts of the food material b, and then by carrying out processes mentioned below.

| | |
|---|---|
| food material b | 100 parts |
| whole egg | 10 parts |
| butter | 5 parts |
| fresh yeast | 3 parts |
| water | 155 parts |

The ingredients, except for the butter, were mixed at a low speed for 2 minutes, then at a medium speed for 3 minutes, and then at a high speed for 1 minute. Subsequently, the mixture was further mixed with addition of the butter at a low speed for 1 minute, then at a medium speed for 3 minutes, and then at a high speed for 3 minutes, while the kneading temperature was 27° C. Furthermore, the dough was fermented at 35° C. for 30 minutes, then was divided into pieces of 70 g each, and then rest for a bench time of 25 minutes. After that, the divided dough was subjected to 60-minute final proof at 38° C. and at 85% relative humidity, and then was baked at 210° C. for 10 minutes.

COMPARATIVE EXAMPLE 3

As Comparative Example 3, a food material c was obtained by replacing the food material B of the Example 2 with a 1-kg mixture of 50 parts wheat protein and 50 parts roasted fusuma bran with addition of 3-g psyllium husk powder as Table 3 given below shows. A bread roll was obtained by adding ingredients in the following proportions to 100 parts of the food material c, and then by carrying out processes mentioned below.

| | |
|---|---|
| food material c | 100 parts |
| whole egg | 10 parts |
| butter | 5 parts |
| fresh yeast | 3 parts |
| water | 155 parts |

The ingredients, except for the butter, were mixed at a low speed for 2 minutes, then at a medium speed for 3 minutes, and then at a high speed for 1 minute. Subsequently, the mixture was further mixed with addition of the butter at a low speed for 1 minute, then at a medium speed for 3 minutes, and then at a high speed for 3 minutes, while the kneading temperature was 27° C. Furthermore, the dough was fermented at 35° C. for 30 minutes, then was divided into pieces of 70 g each, and then rest for a bench time of 25 minutes. After that, the divided dough was subjected to 60-minute final proof at 38° C. and at 85% relative humidity, and then was baked at 210° C. for 10 minutes.

COMPARATIVE EXAMPLE 4

As Comparative Example 4, a croissant was obtained by adding ingredients in the following proportions to 100 parts of the food material c according to the Comparative Example 3 as Table 3 given below shows, and then by carrying out processes mentioned below.

| | |
|---|---|
| food material c | 100 parts |
| whole egg | 10 parts |
| butter | 5 parts |
| fresh yeast | 3 parts |
| roll-in butter | 50 parts |
| water | 155 parts |

The ingredients, except for the butter, were mixed at a low speed for 2 minutes, and then at a medium speed for 3 minutes. Subsequently, the mixture was further mixed with addition of the butter at a low speed for 1 minute, and then at a medium speed for 3 minutes, while dough was cooled to make the kneading temperature be at 24° C. Furthermore, the dough was folded into thirds three times for rolling-in, and then was divided into pieces of 70 g each. After that, the divided dough was subjected to 60-minute final proof at 30° C. and at 75% relative humidity, and then was baked at 210° C. for 10 minutes.

COMPARATIVE EXAMPLE 5

As Comparative Example 5, cookies were obtained by adding ingredients in the following proportions to 100 parts of the food material c according to the Comparative Example 3 as Table 3 given below shows, and then by carrying out processes mentioned below.

| | |
|---|---|
| food material F | 100 parts |
| whole egg | 100 parts |
| butter | 90 parts |
| dolomite | 1 part |
| sucralose | 0.06 parts |
| acesulfame pottasium | 0.06 parts |

Dough was prepared by mixing the liquid whole egg and the butter, and then further mixing completely with addition of the other ingredients. The dough was rolled out to a sheet, and cut out with a certain predetermined cookie cutter (15 g each). The cut-out dough rest for a bench time of approximately an hour, and then was baked at 180° C. for 25 minutes.

COMPARATIVE EXAMPLE 6

As Comparative Example 6, Fresh udon was obtained by adding 45 parts saline solution (8 wt % concentration) to 100 parts of the food material c according to the Comparative Example 3 as Table 3 given below shows, and then by carrying out preparation processes mentioned below.

Preparation Processes

| | |
|---|---|
| mixing | 10 minutes |
| laminating | |
| maturing | 30 minutes |
| flattening | |
| cutting | with No. 12 cutter (square), width: 2.5 mm, thickness: 1.6 mm |

TABLE 3

| | Comparative Example 1 | Comparative Example 2 | Comparative Example 3 | Comparative Example 4 | Comparative Example 5 | Comparative Example 6 |
|---|---|---|---|---|---|---|
| wheat protein | 50 | 50 | 50 | 50 | 50 | 50 |
| fresh fusuma bran | 50 | — | — | — | — | — |
| roasted fusuma bran | — | 50 | 50 | 50 | 50 | 50 |
| psyllium husk powder | — | — | 0.3 | 0.3 | 0.3 | 0.3 |
| | bread roll | bread roll | bread roll | croissant | cookie | fresh udon (noodle) |

Assessment

An assessment was carried out on the bread rolls and croissants produced in Examples 1 to 8, and 11 to 15, and in Comparative Examples 1 to 4. The assessment was done by eight panelists regarding the appearance, crumb, taste, scent, texture and bread-making property of each of the bread rolls and croissants. For each item, 5 points were given to the highest assessment while 1 point to the lowest. For each item, the assessments of the eight panelists were represented numerically by their average value. The results are shown in Table 4A, Table 4B, Table 4C and Table 5.

TABLE 4A

| | appearance | crumb | scent | texture | taste | bread-making property |
|---|---|---|---|---|---|---|
| Example 1 | 3.5 not flat | 3.6 improved mesh | 3.5 a little fusuma smell | 3.8 not dry | 3.0 a little unsavory taste of fusuma | 4.0 sagging of dough improved |

TABLE 4A-continued

|  | appearance | crumb | scent | texture | taste | bread-making property |
|---|---|---|---|---|---|---|
| Example 2 | 4.2 good oven spring | 4.3 extensibility | 3.8 a little fusuma smell | 4.5 not dry soft | 3.2 a little unsavory taste of fusuma | 4.5 no sagging of dough machinable |
| Example 3 | 4.9 volume good oven spring | 4.8 good open crumb | 4.0 slight nuka smell | 4.8 soft crisp | 4.1 unsavory taste of nuka improved | 4.8 no sagging of dough machinable |
| Example 4 | 5.0 volume good oven spring | 5.0 uniform open crumb | 4.6 fermentation aroma | 5.0 soft crisp | 4.3 good aftertaste | 5.0 no sagging of dough machinable |

TABLE 4B

|  | appearance | crumb | scent | texture | taste | bread-making property |
|---|---|---|---|---|---|---|
| Example 5 | 5.0 volume good oven spring | 5.0 uniform open crumb | 5.0 no fusuma smell good aroma | 5.0 soft crisp | 5.0 deep taste with umami | 5.0 no sagging of dough machinable |
| Example 11 | 4.3 volume oven spring | 4.3 good open crumb | 3.8 a little fusuma smell | 4.5 not dry soft | 3.5 a little unsavory taste of fusuma | 4.5 sagging of dough improved machinable |
| Example 12 | 4.0 good oven spring | 4.0 good mesh | 3.5 a little acetic acid smell | 4.3 not dry | 3.0 a little unsavory aftertaste of acetic acid | 4.4 sagging of dough improved machinable |
| Example 13 | 4.0 good oven spring | 4.0 good mesh | 3.7 a little fusuma smell | 4.3 not dry | 3.2 a little unsavory taste of fusuma | 4.4 sagging of dough improved machinable |

TABLE 4C

|  | appearance | crumb | scent | texture | taste | bread-making property |
|---|---|---|---|---|---|---|
| Example 14 | 4.5 good oven spring large volume | 4.5 good open crumb | 3.8 a little fusuma smell | 4.7 not dry | 3.5 a little unsavory taste of fusuma | 4.6 sagging of dough improved machinable |
| Example 15 | 4.2 good oven spring | 4.3 good open crumb | 3.8 a little fusuma smell | 4.6 not dry soft | 3.2 a little unsavory taste of fusuma | 4.5 sagging of dough improved machinable |
| Comparative Example 1 | 1.0 flat | 1.0 totally closed crumb | 1.0 unpleasant fusuma smell | 1.0 hard coarse | 1.0 bitter taste of fusuma | 1.0 unsuitable |
| Comparative Example 2 | 1.8 flat | 1.5 not open crumb | 2.5 fusuma smell | 1.5 dry hard | 2.2 unsavory taste of fusuma | 2.0 dough not consistent |
| Comparative Example 3 | 2.5 flat | 2.0 insufficiently open crumb | 3.5 a little fusuma smell | 2.5 dry | 2.5 unsavory taste of fusuma | 3.0 a little sagging of dough |

TABLE 5

|  | appearance | crumb | scent | texture | taste | bread-making property |
|---|---|---|---|---|---|---|
| Example 6 | 4.0 good oven spring | 4.2 open crumb mesh layered | 3.5 a little fusuma smell | 4.3 soft crisp | 3.0 a little unsavory taste of fusuma | 4.5 no sagging of dough machinable |
| Example 7 | 5.0 good oven spring high rising | 5.0 uniform open crumb | 4.7 fermentation aroma | 5.0 crisp | 4.5 smooth | 5.0 suitable for rolling-in |
| Example 8 | 5.0 good oven spring high rising | 5.0 uniform open crumb | 5.0 no fusuma smell good aroma | 5.0 crisp | 5.0 deep taste with umami | 5.0 suitable for rolling-in |
| Comparative Example 4 | 2.8 flat | 2.5 not layered | 3.5 a little fusuma smell | 3.0 dry | 3.0 a little unsavory taste of fusuma | 2.8 a little sagging of dough |

An assessment was carried out on the cookies produced in Example 9 and in Comparative Example 5. The assessment was done by eight panelists regarding the appearance, crumb, taste, scent, texture and suitability for confectionery making of each of the cookies. For each item, 5 points were given to the highest assessment while 1 point to the lowest. For each item, the assessments of the eight panelists were represented numerically by their average value. The results are shown in Table 6.

The above results show that each of the bread produced in Examples 1 to 8, and 11 to 15 had an improved appearance, crumb, scent, texture, taste and bread-making property in comparison to the bread produced in Comparative Examples 1 to 4. In addition, the cookies produced in Example 9 had an improved appearance, crumb, scent, texture, taste and suitability for confectionery making in comparison to the cookies produced in Comparative Example 5. Moreover, the fresh

TABLE 6

|  | appearance | crumb | scent | texture | taste | suitability for confectionery making |
|---|---|---|---|---|---|---|
| Example 9 | 4.5 | 4.4 uniform | 5.0 no fusuma smell good flavor | 4.7 crisp | 4.0 smooth | 4.5 good consistency of dough |
| Comparative Example 5 | 3.5 | 3.0 a little closed crumb | 3.5 a little fusuma smell | 2.1 coarse | 2.0 not smooth | 3.0 inferior consistency of dough |

An assessment was carried out on the fresh udon produced in Example 10 and in Comparative Example 6. The assessment was done by eight panelists regarding the appearance, crumb, taste, scent, texture and suitability for noodle making of each of the fresh udon after the udon was cooked by boiling water for approximately five minutes. For each item, 5 points were given to the highest assessment while 1 point to the lowest. For each item, the assessments of the eight panelists were represented numerically by their average value. The results are shown in Table 7.

udon (noodle) produced in Example 10 had an improved appearance, crumb, scent, texture, taste and suitability for noodle making in comparison to the fresh udon (noodle) produced in Comparative Example 6. Furthermore, the above-mentioned food products were produced in manufacturing methods clearly different from the methods of manufacturing the food products that have wheat flour as their main ingredients with addition of roasted fusuma bran and the like, that is, from the bread-making method involving the addition

TABLE 7

|  | appearance | noodle string | scent | texture | taste | suitability for noodle making |
|---|---|---|---|---|---|---|
| Example 10 | 4.0 | 4.5 | 3.8 a little fusuma smell | 4.8 elastic | 4.5 good to swallow | 4.5 good extensible dough |
| Comparative Example 6 | 3.0 | 2.5 fragile not elastic | 3.5 a little fusuma smell | 2.0 coarse hard | 2.0 tasteless difficult to swallow | 2.2 inconsistent dough bad workability | of roasted fusuma bran (see JP SH062-22540A), or from the manufacturing method of bread and the like using bread mix (see JP3692199B).

The present invention is applicable to a food material and a food product using such a food material. In particular, the present invention is applicable to a food material which contains wheat protein, a thickening agent and at least one of fusuma bran and nuka bran, but which contains no carbohydrate. Furthermore, the present invention is applicable to health food products produced by using such a food material, and examples of such health food products are bread, cookie, pound cake, sponge cake, udon, soba (buckwheat noodle), and pasta.

The invention thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A bread-like food material which is used for a bread-like food product containing no wheat flour, comprising:
    a wheat protein;
    a thickening stabilizer; and
    at least one of roasted fusuma bran and roasted nuka bran;
    wherein the bread-like food material is substantially devoid of carbohydrate; and
    wherein the thickening stabilizer is at least one of gellan gum, galactomannan, glucomannan, karaya gum, methyl cellulose, carboxymethyl cellulose, and xanthan gum.

2. The bread-like food material as recited in claim 1, further containing a fiber.

3. The bread-like food material as recited in claim 2, wherein the fiber is citrus fiber.

4. The bread-like food material as recited in claim 1, further containing lactic acid ferment.

5. The food bread-like material as recited in claim 4, wherein the lactic acid ferment is made by drying and powderizing microorganisms which belong to yeast *Saccharomyces exiguus* and lactic acid bacteria *Lactobacillus sanfrancisco* having been cultivated in a wheat-flour-dough medium.

6. A food product comprising:
    any one of bread and confectionery made by baking dough prepared by adding sesame paste to a bread like food material;
    wherein the bread-like food material includes a wheat protein, a thickening stabilizer; and at least one of roasted fusuma bran and roasted nuka bran;
    wherein the bread-like food material is substantially devoid of carbohydrate; and
    wherein the thickening stabilizer is at least one of gellan gum, galactomannan, glucomannan, karaya gum, methyl cellulose, carboxymethyl cellulose, and xanthan gum.

* * * * *